United States Patent [19]

Warriner

[11] Patent Number: Plant 5,896

[45] Date of Patent: Mar. 10, 1987

[54] ROSE PLANT JACETTE

[75] Inventor: William A. Warriner, Tustin

[73] Assignee: Jackson & Perkins Company, Medford, Oreg.

[21] Appl. No.: 771,847

[22] Filed: Sep. 3, 1985

[51] Int. Cl.[4] ..... A01H 5/00

[52] U.S. Cl. ..... Plt./14

[58] Field of Search ..... Plt./14

*Primary Examiner*—Robert E. Bagwill

*Attorney, Agent, or Firm*—Manford R. Haxton

[57] ABSTRACT

A hybrid tea rose variety having an attractive high centered white flower with pleasing fragrance coupled with heavy continuous flower production on long straight stems. Also, these flowers occasionally have foliaceous sepals.

1 Drawing Figure

This present invention relates to a new and distinct variety of rose plant of the hybrid tea class which was originated by crossing the variety Bernadette, unpatented, with the variety Coquette, U.S. Plant Pat. No. 4,019.

The primary objective of this breeding was to produce a new rose variety of the hybrid tea class with white flowers suitable for greenhouse cut flower production. This objective was substantially achieved along with other desirable improvements as evidenced by the following unique combination of characteristics which are outstanding in the new variety and which distinguish it from its parents as well as from all other varieties of which I am aware:

1. Heavy and continuous production;
2. Strong pleasing fragrance;
3. Attractive white flower;
4. Occasional foliaceous sepals; and
5. Long straight stems.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with The Royal Horticultural Society Colour Chart except where ordinary dictionary significance of color is indicated.

Parentage:

*Seed parent.*—Bernadette, unpatented.

*Pollen parent.*—Coquette, U.S. Plant Pat. No. 4,019.

Classification:

*Botanical.*—Rosa hybrid.

*Commercial.*—Hybrid tea.

FLOWER

Observations made from specimens grown in a greenhouse at Irvine, Calif. in June.

Blooming habit: Continuous.

Bud:

*Size.*—1½" when petals start to unfurl.

*Form.*—Long, pointed ovoid.

*Color.*—When sepals first divide, Green White Group 157D sometimes tipped with a pale Pink (Red Group 56D). The base of the bud is colored Greyed Yellow 160D.; when half blown, upper side of petals White (Group 155D); lower side of petals, White (Group 155D).

*Sepals.*—Color: Green 137D. Three appendaged sepals normally appendaged and sometimes foliaceous. Two unappendaged sepals hairy edge with glands.

*Receptacle.*—Color: Green 137D. Shape: Funnel. Size: Medium. Surface: Smooth.

*Peduncle.*—Length: Medium. Surface: Smooth, with few glandular. Color: Medium Green. Strength: Stiff.

*Opening.*—Petals recurve slightly and become lightly quilled when fully open.

Open bloom:

*Size.*—Medium. Average open size 4".

*Borne.*—Singly.

*Stems.*—Long.

*Form.*—When first open, high center. Permanence: Flattens.

*Petalage.*—Number of petals under normal conditions: 45-50.

*Color.*—Center of flower: Upper side of petals, White 155D; reverse side of petals, White 155D. Base of petals, Slight yellowish color, Yellow Group 5D. Major color: White.

*Variegation.*—None.

*Discoloration.*—General tonality at end of first day: Remains White 155D. Third day: Remains White 155D.

*Fragrance.*—Strong.

Petals:

*Texture.*—Medium.

*Shape.*—Round to oval, deltoid.

*Form.*—Tips slightly recurved, edges slightly quilled.

*Arrangement.*—Imbricated. Petaloids in center, few.

*Persistence.*—Drop off cleanly.

*Lastingness.*—On the plant, long. As cut flower, long.

Reproductive parts:

*Anthers.*—Many. Color: Yellow. Arrangement: Regular around styles.

*Filaments.*—Color: Greenish.
*Pollen.*—Lemon yellow.
*Styles.*—Color: White.
*Stigmas.*—Color: Red.

PLANT

Form: Bush.
Growth: Vigorous.
Foliage: Number of leaflets on normal mid-stem leaves: 5–7.
*Size.*—Medium.
*Quantity.*—Normal.
*Color.*—New foliage: Reddish turning Green 137A. Old foliage: Green 139A.
Leaflets:
*Shape.*—Broadly elliptic.
*Texture.*—Smooth.
*Edge.*—Serrated.
*Serration.*—Single, small.
*Petiole.*—Rachis: Color: Green. Underside: Rough, with prickles.
*Stipules.*—Medium, bearded.

*Disease resistance.*—Normally resistant to mildew, under normal growing conditions at Irvine, Calif.
Wood:
*New wood.*—Color: Light green. Bark: Smooth.
*Old wood.*—Color: Green. Bark: Smooth.
Prickles:
*Quantity.*—On main canes from base: Ordinary. On laterals from main canes: Ordinary.
*Form.*—Hooked downward.
*Color when young.*—Red.
Small prickles:
*Quantity.*—On main stalks, none. On laterals, none.

I claim:

1. A new and distinct variety of rose plant of the hybrid tea class, substantially as herein shown and described, characterized particularly as to novelty by the unique combination of an attractive high centered white flower with pleasing fragrance coupled with heavy continuous flower production on long straight stems. Also, these flowers occasionally have foliaceous sepals.

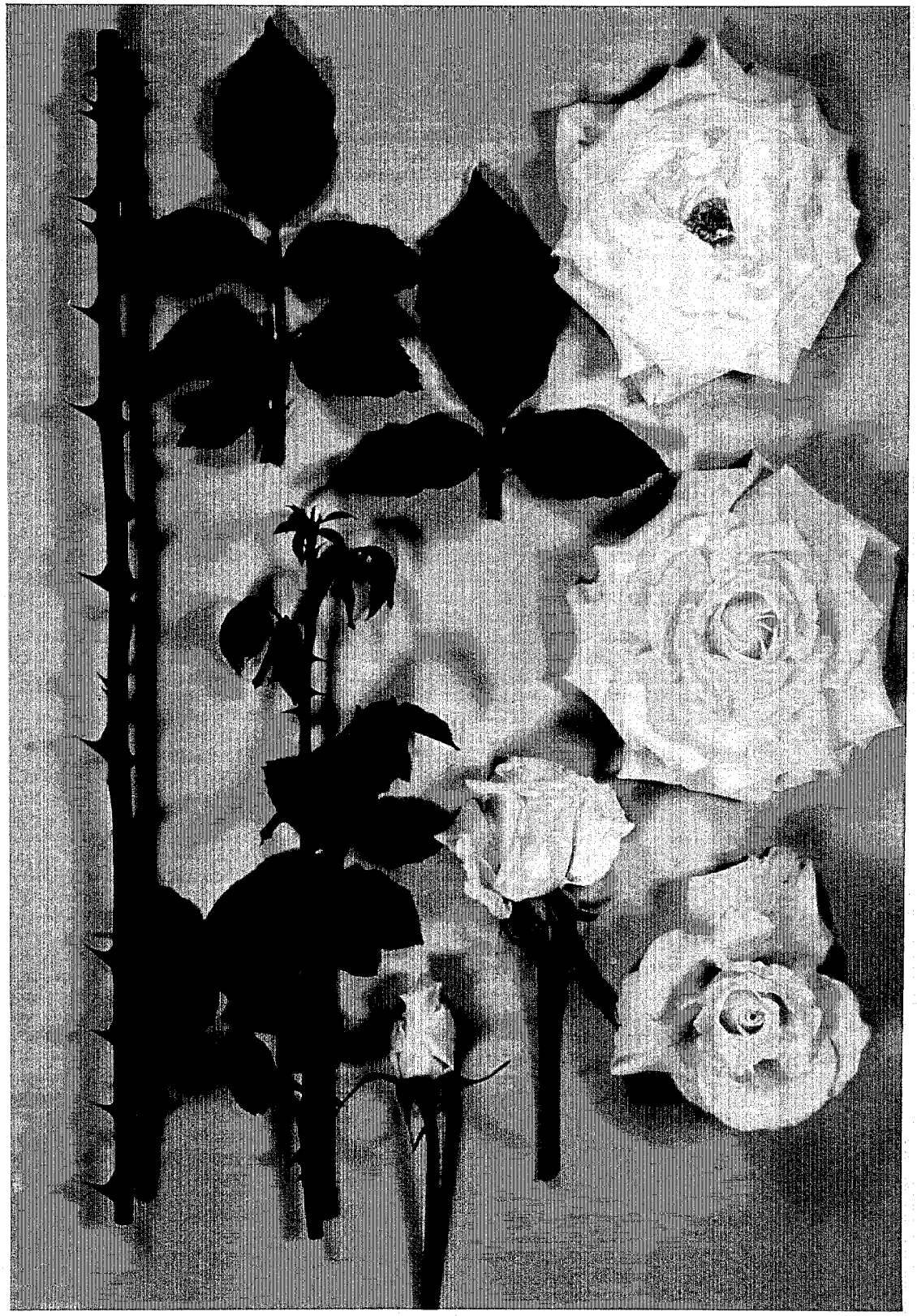

* * * * *